(12) United States Patent
Cotton

(10) Patent No.: US 9,630,222 B2
(45) Date of Patent: Apr. 25, 2017

(54) ALCOHOL PAD SYSTEM, ALCOHOL PAD, AND METHOD FOR CLEANING A MEDICINE VIAL

(71) Applicant: Mary Jane Cotton, Mexia, TX (US)

(72) Inventor: Mary Jane Cotton, Mexia, TX (US)

(73) Assignee: DMJ Products, LLC, Houston, TX (US)

( * ) Notice: Subject to any disclaimer, the term of this patent is extended or adjusted under 35 U.S.C. 154(b) by 0 days.

(21) Appl. No.: 14/566,979

(22) Filed: Dec. 11, 2014

(65) Prior Publication Data

US 2015/0158060 A1   Jun. 11, 2015

Related U.S. Application Data

(60) Provisional application No. 61/914,705, filed on Dec. 11, 2013.

(51) Int. Cl.
| | |
|---|---|
| B43K 5/14 | (2006.01) |
| B08B 9/087 | (2006.01) |
| B65D 75/32 | (2006.01) |
| B65D 75/52 | (2006.01) |
| A61L 2/00 | (2006.01) |
| B65B 55/18 | (2006.01) |
| C11D 7/26 | (2006.01) |
| C11D 17/04 | (2006.01) |

(52) U.S. Cl.
CPC ............ *B08B 9/087* (2013.01); *A61L 2/0088* (2013.01); *B65B 55/18* (2013.01); *B65D 75/325* (2013.01); *B65D 75/527* (2013.01); *C11D 7/261* (2013.01); *C11D 17/049* (2013.01)

(58) Field of Classification Search
CPC ............................ B65D 75/325; B65D 75/527
USPC ........................................ 401/132; 15/104.93
See application file for complete search history.

(56) References Cited

U.S. PATENT DOCUMENTS

| | | | |
|---|---|---|---|
| 3,107,782 A | 10/1963 | Jaroff et al. | |
| 4,427,115 A | 1/1984 | Laipply | |
| 4,893,956 A | 1/1990 | Wojcik et al. | |
| 4,896,768 A | 1/1990 | Anderson | |
| 5,046,608 A * | 9/1991 | Laipply ................. | A47K 10/16 206/209 |
| 5,242,433 A | 9/1993 | Smith et al. | |
| 6,326,069 B1 | 12/2001 | Barnett et al. | |

(Continued)

FOREIGN PATENT DOCUMENTS

| | | |
|---|---|---|
| EP | 0543406 A1 | 5/1993 |
| EP | 0953303 A1 | 11/1999 |

(Continued)

OTHER PUBLICATIONS

PCT International Search Report for PCT/US2014/069683, Mar. 12, 2015.

*Primary Examiner* — Jennifer C Chiang
(74) *Attorney, Agent, or Firm* — Greenberg Traurig, LLP

(57) ABSTRACT

An alcohol pad system, alcohol pad, and method for cleaning a medicine vial include a pad member treated with alcohol and a projection member also treated with alcohol, disposed upon the pad member, with the projection member extending upwardly from the pad member, and the pad member and projection member are adapted to clean, or sanitize, the top of a medicine vial which includes a metal portion and a rubber insert portion disposed within the metal portion of the top of the medicine vial.

21 Claims, 2 Drawing Sheets

(56) References Cited

U.S. PATENT DOCUMENTS

| | | | |
|---|---|---|---|
| 8,262,305 B2 | 9/2012 | Lam et al. | |
| 8,388,894 B2 * | 3/2013 | Colantonio | A61L 2/18 422/119 |
| 2003/0194426 A1 | 10/2003 | Wendel et al. | |
| 2009/0321283 A1 | 12/2009 | Tourigny | |
| 2010/0296968 A1 | 11/2010 | Cady | |
| 2012/0216359 A1 * | 8/2012 | Rogers | B08B 1/00 15/104.93 |
| 2013/0251439 A1 | 9/2013 | Guzman | |

FOREIGN PATENT DOCUMENTS

| | | |
|---|---|---|
| EP | 1714663 A1 | 10/2006 |
| WO | WO 85/03275 A1 | 8/1985 |
| WO | WO8503275 | 8/1985 |
| WO | WO0154661 | 8/2001 |
| WO | WO 2005/009867 | 2/2005 |

\* cited by examiner

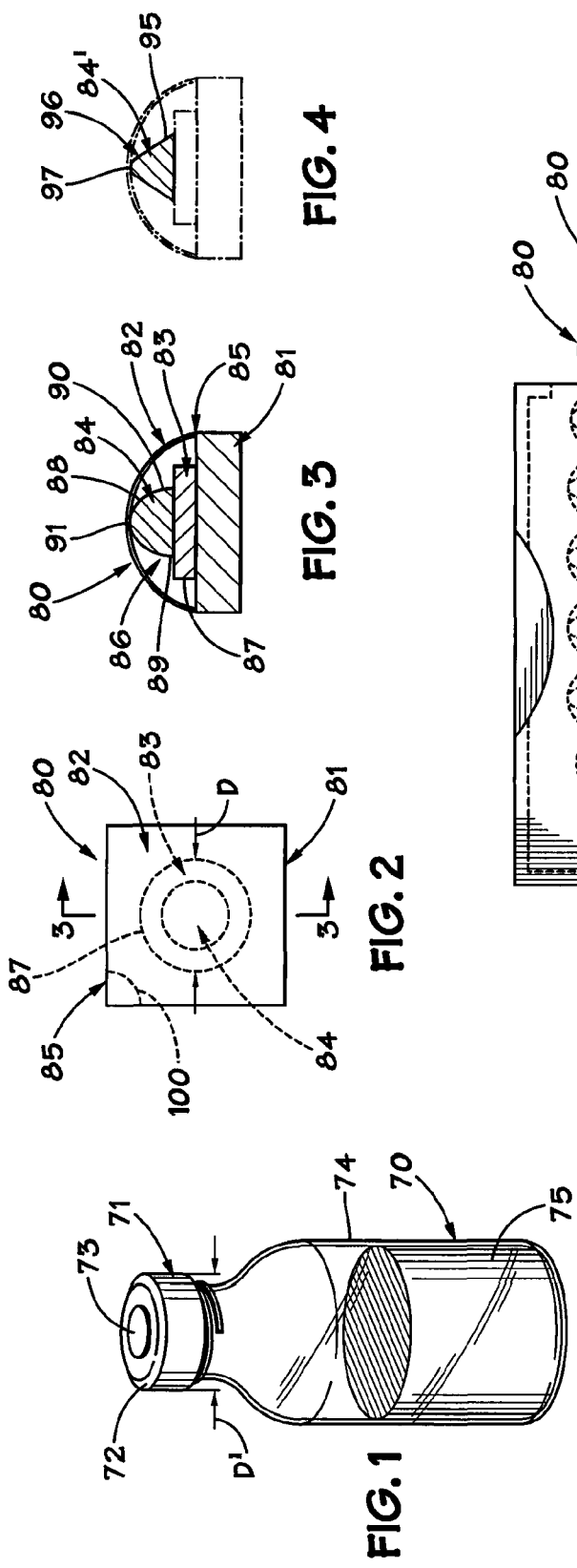

ALCOHOL PAD SYSTEM, ALCOHOL PAD, AND METHOD FOR CLEANING A MEDICINE VIAL

BACKGROUND OF THE INVENTION

1. Related Application

This Application claims the benefit, and priority benefit, of U.S. Patent Application Ser. No. 61/914,705, filed Dec. 11, 2013, entitled "Alcohol Pad System, Alcohol Pad, and Method for Cleaning a Medicine Vial".

2. Field of the Disclosure

This disclosure relates generally to the field of alcohol pads for use in cleaning medical apparatus, including medicine vials.

3. Description of the Related Art

Alcohol pads, or alcohol prep pads, are in widespread use today in hospitals, doctor's offices, and other medical care facilities. Such alcohol prep pads are typically made of an absorbent, non-woven pad material, saturated with 70% isopropyl alcohol. These alcohol prep pads are used as a topical antiseptic prior to giving a patient an injection, and are individually packaged. Each time an alcohol prep pad is needed, the individual package, or packet, is torn open to permit medical personnel to grasp an alcohol prep pad for use. The alcohol prep pad may be used to clean the patient's skin in the general location where the injection is to be made. Such alcohol prep pads may also be used to clean, or sanitize, the top of a medicine vial containing the medicine to be injected into a patient, or other medical apparatus such as IV ports.

Alcohol prep pads are used to prevent hospital associated infections ("HAIs"). According to the Centers for Disease Control, HAIs are infections that patients acquire during the course of receiving health care treatment for other conditions. Infections related to medical care can be devastating and even deadly. HAIs are an important public health problem, and it has been estimated that approximately one out of every 20 hospitalized patients will contract an HAI.

HAIs can be caused by not using aseptic techniques when preparing a medicine vial for use with a patient, as nurses may rub the top of the medicine vial with their bare finger while not wearing gloves, and bacteria on the nurse's finger may wick through to the top of the vial. When inserting a syringe into the medicine vial to obtain the necessary dosage of the medicine to be injected into the patient, such bacteria may be transferred to the needle of the syringe if the medicine vial has not been properly cleaned, and into the patient during the medicine injection, which can cause a HAI.

BRIEF SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the invention or to delineate the scope of the invention. Its sole purpose is to present some concepts in a simplified form as a prelude to the more detailed description that is discussed later.

In one illustrative embodiment, an alcohol pad may include a base member, a cover member disposed over, and in a spaced relationship from a portion of the base member; a pad member treated with alcohol and disposed upon the base member; and a projection member treated with alcohol, disposed upon the pad member, the projection member extending upwardly from the pad member toward the cover member. The cover member may have an outer edge surface sealingly and removably attached to the base member, and the cover member and the base member may define a container for the pad member and the projection member. The projection member may have an upper and a lower end and a base portion extending upwardly from the lower end to the upper end of the projection member, and a tip portion may be disposed at the upper end of the projection member. The tip portion of the projection member may have a rounded configuration. The pad member and the projection member may be formed of an absorbent material which is treated with alcohol by the saturation of the absorbent material with the alcohol. A plurality of alcohol pads may be disposed upon a flexible strip member, and the strip member and alcohol pads may be disposed within a dispenser container.

In another illustrative embodiment, an alcohol pad system may include a base member; and a plurality of alcohol pads, at least some of the alcohol pads including a cover member disposed over, and in a spaced relationship from a portion of the base member, a pad member treated with alcohol and disposed upon the base member, and a projection member treated with alcohol, disposed upon the pad member, each projection member extending upwardly from the pad member toward the cover member. Each cover member may have an outer edge surface sealingly and removably attached to a portion of the base member, and the cover member and a portion of the base member may define a container for each pad member and projection member. Each projection member may have an upper and a lower end and a base portion extending upwardly from the lower end to the upper end of the projection member, and a tip portion may be disposed at the upper end of the projection member. The cover member may include a tab member, and the pad member and projection members may be formed of an absorbent material which is treated with alcohol by the saturation of the absorbent material with the alcohol. The alcohol pads may be disposed upon the base member in a spaced relationship from each other in a grid configuration.

In another illustrative embodiment, a method for cleaning a medicine vial having a top including a metal portion and a rubber insert disposed in the metal portion of the top may include: providing an alcohol pad having a base member, a cover member disposed over, and in a spaced relationship from a portion of the base member, a pad member treated with alcohol and disposed upon the base member, and a projection member treated with alcohol, disposed upon the pad member, the projection member extending upwardly from the pad member toward the cover member; removing the cover member from the alcohol pad; pressing the rubber insert in the metal portion of the top of the medicine vial against the projection member, whereby the alcohol of the projection member cleans the rubber insert; and pressing the metal portion of the top against the pad member, whereby the alcohol of the pad member cleans the metal portion of the top. The medicine vial may be rotated while the rubber insert is being pressed against the projection member and the metal portion of the top is pressed against the pad member.

BRIEF DESCRIPTION OF THE DRAWING

The present alcohol pad system, alcohol pad, and method for cleaning a medicine vial may be understood by reference to the following description taken in conjunction with the accompanying drawing, in which:

FIG. 1 is a perspective view of a conventional medicine vial with which the present alcohol pad system, alcohol pad, and method for cleaning a medicine vial may be used;

FIG. 2 is a top view of an illustrative embodiment of the present alcohol pad;

FIG. 3 is a partial cross-sectional view of the alcohol pad taken along lines 3-3 of FIG. 2;

FIG. 4 is a side view of another illustrative embodiment of a projection member for use with the alcohol pad of FIG. 2;

FIG. 5 is a front view of a dispenser container for a plurality of alcohol pads as shown in FIG. 2;

Figure 6:
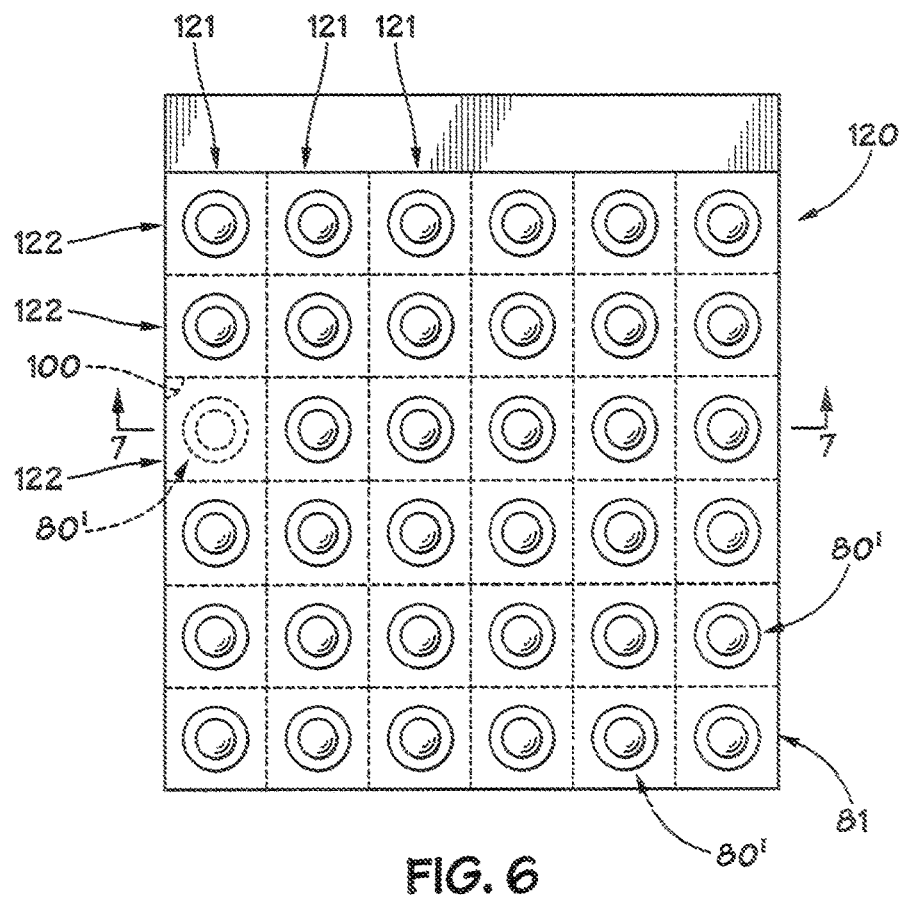
FIG. 6 is a top view of an illustrative embodiment of the present alcohol pad system.

While certain embodiments of the present alcohol pad system, alcohol pad, and method for cleaning a medicine vial will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the invention as defined by the appended claims. In the drawing figures, which are not to scale, the same reference numerals are used throughout the description and in the drawing figures for components and elements having the same structure, and primed reference numerals are used for components and elements having a similar function and construction to those components and elements having the same unprimed reference numerals.

DETAILED DESCRIPTION OF THE SPECIFIC EMBODIMENTS

With reference to FIG. 1, a conventional medicine vial 70 is shown and includes a top 71 which includes a metal portion 72 and a rubber insert 73 disposed in the metal portion 72 of the top 71. Medicine vial 70 includes a glass container 74 which holds the medicine 75 to be injected into a patient. A needle (not shown) of a conventional syringe (not shown) may be inserted into the rubber insert 73 of the top 71, and in a conventional manner the medicine 75 is withdrawn into the syringe. The Centers for Disease Control and Prevention recommend that the top 71 of the medicine vial 70 be cleaned for 15 seconds.

With reference to FIGS. 2 and 3, an illustrative embodiment of the present alcohol pad 80 generally comprises: a base member 81; a cover member 82 disposed over, and in a spaced relationship, from a portion of the base member 81; a pad member 83 treated with alcohol and disposed upon the base member 81; and a projection member 84 treated with alcohol, disposed upon the pad member 83, with the projection member extending upwardly from the pad member 83 toward the cover member 82. The cover member 82 has an outer edge surface 85 sealingly and removably attached to the base member 81, and the cover member 82 and base member 81 define a container, or housing, 86 for the pad member 83 and projection member 84.

Still with reference to FIGS. 2 and 3, base member 81 may be formed of any suitable material which permits it to be used as a base member 81 for alcohol pad 80, including having the requisite strength characteristics to function as a base member 81 to support the pad member 83 and projection member 84 upon base member 81. Additionally, base member 81 is preferably: resistant to the alcohol used to treat projection member 84 and pad member 83; moisture resistant to contain and maintain the alcohol within the container, or housing 86, in combination with cover member 82, when pad member 83 and projection member 84 are disposed within container, or housing, 86; and capable of maintaining the sterile nature of the alcohol treated pad member 83 and projection member 84. Suitable materials for use as base member 81 include, but are not limited to, various plastics, metal foils and films, and plastic or metal covered paper and cardboard materials, or other materials having the foregoing described characteristics.

Cover member 82 also must also have the previously described characteristics of base member 81; as well as permits cover member 82 to overlie the projection member 84 and pad member 83, and to be sealingly and removably attached to base member 81. Cover member 82 may be made of any suitable rigid or flexible plastic material, such as any suitable plastic film, or any suitable metal foil, or other materials which permits cover member 82 to function as a container, or housing 86 for the pad member 83 and projection member 84.

Still with reference to FIGS. 2 and 3, pad member 83 may be made of any suitable material which may be treated with alcohol and used to clean top 71 of medicine vial 70 of FIG. 1, or other medical apparatus. Preferably pad member 83 is made of an absorbent material which may be treated with alcohol by the saturation of the absorbent material with the alcohol (not shown). Pad member 83 may be made of an absorbent woven, or non-woven, material which could be a natural material, such as cotton or a sponge material, or a synthetic material made of suitable plastic, including a synthetic sponge-like material. Preferably, the material used to make pad member 83, after being treated with alcohol, may be compressed upon top 71 of medicine vial 70 being pressed against pad member 83, as will be hereinafter described in greater detail. Projection member 84 may be formed of the same type of materials as previously described in connection with pad member 83. Pad member 83 may be fixedly secured to base member 81 in any suitable manner, as by use of a small amount of adhesive, so pad member 83 is fixedly secured to base member 81. Similarly, projection member 84 may be fixedly secured to pad member 83 by a suitable adhesive. Alternatively, pad member 83 and projection member 84 may be formed as an integral structure whereby no adhesive is required to be used between pad member 83 and projection member 84. Cover member 82 may be sealingly and removably attached to base member 81 in any suitable manner, as by the use of adhesive, or by heat sealing cover member 82 to base member 81, whereby outer edge surface 85 of cover member 82 is sealingly and removably attached to the base member 81. Cover member 82 may contact the upper end of projection member 84 as shown in FIG. 3, or cover member 82 may be disposed in a spaced relationship from the upper end of the projection member 84.

Still with reference to FIGS. 2 and 3, pad member 83 may preferably have a circular shaped outer wall surface 87 and the diameter D of pad member 83 is preferably larger than the diameter D' of the top 71 of medicine vial 70 of FIG. 1. Of course, pad member 84 could have other configurations other than circular, such as square, hexagonal, etc., all of which are preferably larger than the top 71 of medicine vial 70, or larger than the shape of the medical apparatus being cleaned with alcohol pad 80. The cover member 82 shown in FIGS. 2 and 3 is an opaque material, whereby pad member 83 and projection member 84 are shown in phantom lines in FIG. 2. If desired, cover member 82 could also be made of a suitable clear or transparent material.

Still with reference to FIGS. 2 and 3, projection member 84 may have an upper, end 88, and a lower end 89 and a base portion 90 extends upwardly from the lower end 89 to the upper end 88 of projection member 84. A tip portion 91 is disposed at the upper end 88 of the projection member 84. The tip portion 91 may have a rounded configuration, and base portion 90 may have a cylindrical configuration.

Alternatively, as shown in FIG. 4, projection member 84' may have a cone-shaped outer wall surface 95 and the cone-shaped outer wall surface 95 may have an upper end 96 having a rounded tip 97. As will be hereinafter described in greater detail, projection member 84, 84' is used to clean the rubber insert 73 of top 71 of medicine vial 70 of FIG. 1, whereby the rounded tip 91, 97 of projection 84, 84' has a size that generally conforms to the size of the rubber insert 73, which is intended to be cleaned. Of course, other cross-sectional configurations for projection member 84, 84' could be utilized, such as square, hexagonal, etc., provided the upper end 88, 96, of projection member 84, 84' is disposed in a spaced relationship from base member 83 and projection member 84, 84' generally extends upwardly from base member 83.

As seen in FIG. 2, alcohol pad 80 preferably includes a tab member 100 (shown in phantom lines in FIG. 2). Tab member 100 of cover member 82 permits a user of alcohol pad 80 to grasp the tab member 100 and to pull the tab member 100, which is part of cover member 82, to remove the cover member 82 from the base member 81, to expose the projection member and base member 83 so that they may be used to clean or sanitize the top 71 of a medicine vial 70 as shown in FIG. 1, or other types of medical apparatus, such as intravenous lines, central lines, or ports. After cover member 82 has been removed from the base member 71 of alcohol pad 80, a nurse, doctor, or other person may then press the rubber insert 73 in the metal portion 72 of the top 71 of medicine vial 70 against the projection member 84, 84', whereby the alcohol of the projection member 84, 84' may clean, or sanitize, the rubber insert 73. By pressing the metal portion 72 of top 71 against the pad member 83, the alcohol of the pad member 83 may clean the metal portion 72 of the top 71 of medicine vial 70 of FIG. 1 or other medical apparatus desired to be cleaned. The nurse or doctor may rotate the medicine vial 70 with respect to the alcohol pad 80 while the rubber insert 72 is being pressed against the projection member 84, 84' and the metal portion 72 of the top 71 is pressed against the pad member 83. The alcohol pad 80 may be held by the nurse or doctor in his or her hand while cleaning the medicine vial 70 as previously described, or alternatively, the alcohol pad 80 may be placed upon and held against a flat surface, such as a table or bench, and the medicine vial 70 could be pressed against alcohol pad 80 as previously described. The projection member also serves as a guide member or positioning device to be received within the rubber insert 73 of top 71 to keep the proper spatial relationship between the top 71 and alcohol pad 80 so that both the rubber insert 73 and metal portion 72 of top 71 are properly cleaned and to prevent the top 71 from sliding off pad 80 while it is being cleaned.

With reference to FIG. 5, a plurality of alcohol pads 80 may be disposed upon a flexible strip member 111 formed of a suitable plastic or paper material, or other similar material, and the strip member 111 and alcohol pads 80 may be disposed within a dispenser container 110. As an alcohol pad 80 is desired to be used, the strip member 111 may be pulled from the dispenser container, and an alcohol pad 80 which is removably secured to flexible strip 111 may be pulled, or pealed, off strip member 111, and thereafter alcohol pad 80 may be used as previously described.

Figure 7:
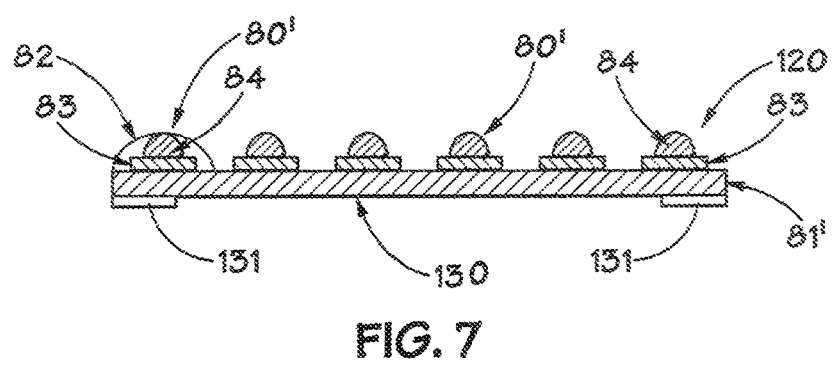
FIG. 7 is a partial cross-sectional view of the alcohol pad system taken along lines 7-7 of FIG. 6.

With reference to FIGS. 6 and 7, an illustrative embodiment of an alcohol pad system 120 is illustrated. The alcohol pad system 120 is generally comprised of a base member 81', and a plurality of alcohol pads 80'. At least some of the alcohol pads 80' include a cover member 82 disposed over, and in a spaced relationship from a portion of the base member 81'. At least some of the alcohol pads 80' also include a pad member 83 treated with alcohol and disposed upon the base member 81'. At least some of the alcohol pads 80' also include a projection member 84 treated with alcohol, disposed upon the pad member 83, with each projection member 84 extending upwardly from a pad member 83 toward the cover member 82. In general, the alcohol pad system 120 includes a plurality of the alcohol pads 80, previously described in connection with FIGS. 2-4, with base member 81' being larger in size to accommodate the plurality of alcohol pads 80', whereby the alcohol pads 80' are disposed upon the base member 81' in a spaced relationship from each other in a grid configuration as shown in FIGS. 6 and 7. The grid configuration includes a plurality of columns 121 and rows 122 as shown in FIG. 6 and denoted by the phantom lines between rows and columns. If desired, the grid configuration could be staggered, whereby the alcohol pads 80' are still disposed upon the base member 81' in a spaced relationship from each other; however, the alcohol pads 80' of one row 122 does not have to be disposed directly above another alcohol pad 80' in a lower row 122 as viewed in FIG. 6. All of the alcohol pads 80' illustrated in FIGS. 6 and 7 are shown with their cover members 82 having been removed, with the exception of the alcohol pad 80' of the far left column 121 in the third row 122 from the top of pad system 120, which alcohol pad 80' is shown to still have cover member 82 being disposed over the pad member 83 and projection member 84, whereby pad member 83 and projection member 84 are shown in phantom lines in FIG. 6.

Still with reference to FIGS. 6 and 7, each cover member 82 includes a tab member 100 as previously described, to permit removal of cover member 82 from base member 81'. The cover members 82 could be individually, sealingly and removably attached to a portion of base member 81' associated with each alcohol pad 80', or alternatively, a single sheet of material could be utilized to form the cover members 82, with the single sheet of material having perforations as indicated by the phantom lines in FIG. 6, which phantom lines also denote the rows and columns 121, 122.

If desired, the base member 81 could be provided on its lower surface 130 with a plurality of grip members, or skid members, 131. When alcohol pad system 120 is utilized, it would likely be disposed upon a counter in the medication room of a hospital or doctor's office, or upon a medication cart. A cover member 82 would be removed from alcohol pad system 120, each time it is desired to clean the top 71 of a medicine vial 70 of FIG. 1. The top 71 of medicine vial 70 would be cleaned in a manner previously described, wherein a nurse or doctor or other person, would press top 71 of medicine vial 70 upon an alcohol pad 80' in the manner previously described to clean insert 73 and the metal portion 72 of top 71. During such cleaning procedure, the grip members, or skid members 131, would tend to prevent the alcohol pad system 120 from moving or skidding on the counter or flat surface upon which base member 81 is placed.

Specific embodiments of the present alcohol pad system, alcohol pad, and method for cleaning a medicine vial have been described and illustrated. It will be understood to those skilled in the art that changes and modifications may be made without departing from the spirit and scope of the inventions defined by the appended claims.

I claim:

1. An alcohol pad for cleaning a top of a medicine vial having an insert in the top, comprising:
   a base member having an upper surface;
   a cover member disposed over, and in a spaced relationship from a portion of the upper surface of the base member, the cover member having an outer edge surface sealingly and removably attached to the upper surface of the base member;
   a pad member treated with alcohol and disposed upon the upper surface of the base member;
   a projection member treated with alcohol, disposed upon the pad member, the projection member extending upwardly from the pad member toward the cover member; and
   the cover member and the upper surface of the base member defining a container for the pad member and the projection member.

2. The alcohol pad of claim 1, wherein the pad member has a circular shaped outer wall surface.

3. The alcohol pad of claim 1, wherein the projection member is also a guide member adapted to be received within the insert in the top of the medicine vial, and has a cone shaped outer wall surface.

4. The alcohol pad of claim 3, wherein the cone shaped outer wall surface has an upper end having a rounded tip.

5. The alcohol pad of claim 1, wherein the projection member is also a guide member adapted to be received within the insert in the top of the medicine vial, and has an upper and a lower end and a base portion extending upwardly from the lower end to the upper end of the projection member, and a tip portion is disposed at the upper end of the projection member.

6. The alcohol pad of claim 5, wherein the tip portion of the projection member has a rounded configuration.

7. The alcohol pad of claim 1, wherein the cover member includes a tab member.

8. The alcohol pad of claim 1, wherein the pad member and projection member are formed of an absorbent material which is treated with alcohol by the saturation of the absorbent material with the alcohol.

9. The alcohol pad of claim 1, wherein a plurality of alcohol pads are disposed upon a flexible strip member, and the strip member and alcohol pads are disposed within a dispenser container.

10. An alcohol pad system for cleaning a top of a medicine vial having an insert in the top, comprising:
    a base member having an upper surface;
    a plurality of alcohol pads, whereby at least some of the pads are disposed upon the base member in a spaced relationship from each other in a grid configuration, each of the at least some pads comprises a pad member treated with alcohol and disposed upon the upper surface of the base member and a projection member treated with alcohol, disposed upon the pad member, each projection member extending upwardly from a pad member toward a cover member, the cover member disposed over, and in a spaced relationship from a portion of the upper surface of the base member, and each cover member has an outer edge surface sealingly and removably attached to the upper surface of the base member, and each cover member and the upper surface of the base member define a container for each pad member and projection member.

11. The alcohol pad system of claim 10, wherein each pad member has a circular shaped outer wall surface.

12. The alcohol pad system of claim 10, wherein each projection member is also a guide member adapted to be received within the insert in the top of the medicine vial, and has a cone shaped outer wall surface.

13. The alcohol pad system of claim 12, wherein the cone shaped outer wall surface has an upper end having a rounded tip.

14. The alcohol pad system of claim 10, wherein each projection member is also a guide member adapted to be received within the insert in the top of the medicine vial, and has an upper and a lower end and a base portion extending upwardly from the lower end to the upper end of the projection member, and a tip portion is disposed at the upper end of the projection member.

15. The alcohol pad system of claim 14, wherein the tip portion of the projection member has a rounded configuration.

16. The alcohol pad system of claim 10, wherein the cover member includes a tab member.

17. The alcohol pad system of claim 10, wherein the pad member and projection member are formed of an absorbent material which is treated with alcohol by the saturation of the absorbent material with the alcohol.

18. The alcohol pad system of claim 1, wherein the alcohol pads are disposed upon the base member in a spaced relationship from each other in a grid configuration.

19. The alcohol pad system of claim 1, wherein upper surface of the base member is flat.

20. The alcohol pad system of claim 10, wherein the upper surface of the base member is flat.

21. The alcohol pad system of claim 10, wherein the base member has a lower surface and a plurality of grip members are provided on the lower surface.

* * * * *